United States Patent
Desmeules et al.

(10) Patent No.: US 10,806,739 B2
(45) Date of Patent: Oct. 20, 2020

(54) USE OF N-DESMETHYLCLOBAZAM IN THE TREATMENT OF CHRONIC PAIN DISORDERS AND RELATED METHODS

(71) Applicants: LES HOPITAUX UNIVERSITAIRES DE GENEVE, Geneva (CH); UNIVERSITAT ZURICH, Zurich (CH); UNIVERSITE DE GENEVE, Geneva (CH)

(72) Inventors: Jules Desmeules, Geneva (CH); Hanns Ulrich Zeilhofer, Zurich (CH); Marie Besson, Geneva (CH); Youssef Daali, Chene-Bourg (CH); Alain Matthey, Coppet (CH); William T. Ralvenius, Zurich (CH)

(73) Assignees: LES HOPITAUX UNIVERSITAIRES DE GENEVE, Geneva (CH); UNIVERSITAT ZURICH, Zurich (CH); UNIVERSITE DE GENEVE, Geneva (CH)

( * ) Notice: Subject to any disclaimer, the term of this patent is extended or adjusted under 35 U.S.C. 154(b) by 0 days.

(21) Appl. No.: 15/555,227

(22) PCT Filed: Mar. 2, 2016

(86) PCT No.: PCT/IB2016/051158
§ 371 (c)(1),
(2) Date: Sep. 1, 2017

(87) PCT Pub. No.: WO2016/139586
PCT Pub. Date: Sep. 9, 2016

(65) Prior Publication Data
US 2018/0161341 A1 Jun. 14, 2018

(30) Foreign Application Priority Data
Mar. 2, 2015 (EP) .................. 15157219

(51) Int. Cl.
*A61K 31/551* (2006.01)
*A61P 25/00* (2006.01)
*A61K 45/06* (2006.01)

(52) U.S. Cl.
CPC ............ *A61K 31/551* (2013.01); *A61K 45/06* (2013.01); *A61P 25/00* (2018.01)

(58) Field of Classification Search
CPC ........ A61K 31/551; A61K 45/06; A61P 25/00
See application file for complete search history.

(56) References Cited

PUBLICATIONS

Verdu et al, Drugs, 68, 18, 2611-2632 (Year: 2008).*
Atack, J. R. et al. "TPA023 [7-(1,1-Dimethylethyl)-6-(2-ethyl-2H-1,2,4-triazol-3-ylmethoxy)-3-(2-fluorophenyl)-1,2,4-triazolo[4,3-b]pyridazine], an Agonist Selective for $\alpha 2$- and $\alpha 3$-Containing $GABA_A$ Receptors, Is a Nonsedating Anxiolytic in Rodents and Primates" *The Journal of Pharmacology and Experimental Therapeutics*, 2006, pp. 410-422, vol. 316, No. 1.
Besson, M. et al. "Antihyperalgesic Effect of the $GABA_A$ Ligand Clobazam in a Neuropathic Pain Model in Mice: A Pharmacokinetic—Pharmacodynamic Study" *Basic & Clinical Pharmacology & Toxicolgy*, 2013, pp. 192-197, vol. 112.
Besson, M. et al. "GABAergic modulation in central sensitization in humans: a randomized placebo-controlled pharmacokinetic—pharmacodynamic study comparing clobazam with clonazepam in healthy volunteers" *Pain*, Mar. 2015, pp. 397-404, vol. 156, No. 3.
Corrigan, R. et al. "Clonazepam for neuropathic pain and fibromayalgia in adults (Review)" *Cochrane Database of Systematic Reviews*, 2012, pp. 1-15, Issue 5, Art. No. CD009486.
Crestani, F. et al. "Trace fear conditioning involves hippocampal $\alpha_5$ $GABA_A$ receptors" *PNAS*, Jun. 25, 2002, pp. 8980-8985, vol. 99, No. 13.
Déglon, J. et al. "Automated system for on-line desorption of dried blood spots applied to LC/MS/MS pharmacokinetic study of flurbiprofen and its metabolite" *Journal of Pharmaceutical and Biomedical Analysis*, 2011, pp. 359-367, vol. 54.
Dellemijn, P. L. I. et al. "Randomised double-blind active-placebo-controlled crossover trial of intravenous fentanyl in neuropathic pain" *The Lancet*, Mar. 15, 1997, pp. 753-758, vol. 349.
Dias, R. et al. "Evidence for a Significant Role of $\alpha 3$-Containing $GABA_A$ Receptors in Mediating the Anxiolytic Effects of Benzodiazepines" *The Journal of Neuroscience*, Nov. 16, 2005, pp. 10682-10688, vol. 25, No. 46.
Gremeau-Richard, C. et al. "Topical clonazepam in stomatodynia: a randomised placebo-controlled study" *PAIN*, 2004, pp. 51-57, vol. 108.
Griebel, G. et al. "50 years of hurdles and hope in anxiolytic drug discovery" *Nature Reviews Drug Discovery*, Sep. 2013, pp. 667-687 (numbered as pp. 1-46), vol. 12, No. 9.
Jensen, H. S. et al. "Clobazam and Its Active Metabolite N-desmethylclobazam Display Significantly Greater Affinities for $\alpha_2$- versus $\alpha_1$-$GABA_A$—Receptor Complexes" *PLoS ONE*, Feb. 2014, pp. 1-8, vol. 9, Issue 2, e88456.
Löw, K. et al. "Molecular and Neuronal Substrate for the Selective Attenuation of Anxiety" *Science*, Oct. 6, 2000, pp. 131-134, vol. 290.
McKernan, R. M. et al. "Sedative but not anxiolytic properties of benzodiazepines are mediated by the $GABA_A$ receptor $\alpha_1$ subtype" *Nature Neuroscience*, Jun. 2000, pp. 587-592, vol. 3, No. 6.

(Continued)

*Primary Examiner* — Sudhakar Katakam
(74) *Attorney, Agent, or Firm* — Saliwanchik, Lloyd & Eisenschenk (57) ABSTRACT

The present invention is directed to N-desmethylclobazam or any suitable pharmaceutically acceptable thereof useful for the prevention and/or treatment of a chronic pain disorder and related methods and pharmaceutical formulations.

18 Claims, 8 Drawing Sheets

(56) References Cited

PUBLICATIONS

Munro, G. et al. "Developing analgesics by enhancing spinal inhibition after injury: $GABA_A$ receptor subtypes as novel targets" *Trends in Pharmacological Sciences*, Jun. 2009, pp. 453-459, vol. 30, No. 9.

Ralvenius, W. T. et al. "Analgesia and unwanted benzodiazepine effects in point-mutated mice expressing only one benzodiazepine-sensitive $GABA_A$ receptor subtype" *Nature Communications*, Apr. 13, 2015, pp. 1-12, vol. 6, No. 6803.

Ralvenius, W. T. et al. "The clobazam metabolite N-desmethyl clobazam is an α2 preferring benzodiazepine with an improved therapeutic window for antihyperalgesia" *Neuropharmacology*, 2016, pp. 366-375, vol. 109.

Rowbotham, M. C. "Mechanisms of neuropathic pain and their implications for the design of clinical trials" *Neurology*, Dec. 2005, pp. S66-S73, vol. 65, Suppl. 4.

Rudolph, U. et al. "Benzodiazepine actions mediated by specific γ-aminobutyric $acid_A$ receptor subtypes" *Nature*, Oct. 21, 1999, pp. 796-800, vol. 401.

Rudolph, U. et al. "Beyond classical benzodiazepines: Novel therapeutic potential of $GABA_A$ receptor subtypes" *Nature Reviews Drug Discovery*, 2011, pp. 685-697 (numbered as pp. 1-26), vol. 10, No. 9.

Skolnick, P. et al. "Anxioselective Anxiolytics: On a Quest for the Holy Grail" *Trends in Pharmacological Sciences*, Nov. 2012, pp. 611-620 (numbered as pp. 1-18), vol. 33, No. 11.

Suzuki, M. "Role of N-methyl-$_D$-aspartate receptor antagonists in postoperative pain management" *Current Opinion in Anaesthesiology*, 2009, pp. 618-622, vol. 22.

Vuilleumier, P. H. et al. "Evaluation of Anti-Hyperalgesic and Analgesic Effects of Two Benzodiazepines in Human Experimental Pain: A Randomized Placebo-controlled Study" *PLoS ONE*, Mar. 2013, pp. 1-14, vol. 8, Issue 3, e43896.

Wiffen, P. J. et al. "Antiepileptic drugs for neuropathic pain and fibromyalgia—an overview of Cochrane reviews (Review)" *Cochrane Database of Systematic Reviews*, 2013, pp. 1-26, Issue 11, Art. No. CD010567.

Zeilhofer, H. U. et al. "Chronic Pain States: Pharmacological Strategies to Restore Diminished Inhibitory Spinal Pain Control" *Annual Review of Pharmacology Toxicology*, 2012, pp. 111-133, vol. 52.

Written Opinion in International Application No. PCT/IB2016/051158, dated Apr. 22, 2016, pp. 1-5.

Volz, M. et al. "Kinetics and Metabolism of Clobazam in Animals and Man" *Br. J. Clin. Pharmac.*, 1979, pp. 41S-50S, vol. 7.

\* cited by examiner a b

Figure 1

Figure 2 dose (mg/kg) per oral NMDC

USE OF N-DESMETHYLCLOBAZAM IN THE TREATMENT OF CHRONIC PAIN DISORDERS AND RELATED METHODS

CROSS-REFERENCE TO RELATED APPLICATION

This application is the U.S. national stage application of International Patent Application No. PCT/IB2016/051158, filed Mar. 2, 2016.

FIELD OF THE INVENTION

The present invention relates to the use of a metabolite of the benzodiazepine clobazam and compositions thereof in the prophylaxis and/or treatment of chronic pain disorders.

BACKGROUND OF THE INVENTION

While acute pain is a normal sensation triggered in the nervous system to alert the living body to possible injury, chronic pain is characterized by persisting pain signals firing in the nervous system for days, weeks, months, even years. There may have been some triggering event such as sprained back, serious infection, or there may be an ongoing cause of pain such as arthritis, cancer, ear infection, but in some subjects suffering from chronic pain the past injury or the body damage is less evident. Many chronic pain conditions affect older adults. Common chronic pain complaints include headache, low is back pain, or neuropathic pain (pain resulting from damage to the peripheral nerves or to the central nervous system itself). A person may have two or more co-existing chronic pain conditions. Such conditions can include chronic fatigue syndrome, endometriosis, fibromyalgia, inflammatory bowel disease, interstitial cystitis, temporomandibular joint dysfunction, and vulvodynia.

Clinical investigators have found that chronic pain patients often have lower-than-normal levels of endorphins in their spinal fluid and stress would be one factor involved in chronic pain since anxiety, stress, depression, anger, and fatigue interact in complex ways with chronic pain and may decrease the body's production of natural painkillers such as endorphins and the like. Moreover, such negative feelings may increase the level of substances that amplify sensations of pain, causing a vicious cycle of pain for the subject. Even the body's most basic defenses may be compromised by prolonged chronic pain event and there is considerable evidence that unrelenting pain can suppress or depress the immune system.

Pharmacological management of chronic pain is still an unmet medical need. In the light of the recent progress in the understanding of the neurobiology of chronic pain states, mechanism-based approaches have been advocated (Rowbotham, 2005, *Neurology,* 65(12 Suppl 4):S66-73). Diminished synaptic inhibition in the spinal cord has been recognized in the last decade as an important contributor to central sensitization (Zeilhofer et al., 2012, *Annu. Rev. Pharmacol. Toxicol,* 52, 111-33), a key phenomenon in chronic inflammatory and neuropathic pain.

On the therapeutic side, there are only few alternatives (pregabalin, gabapentin, duloxetin and certain opioids) which are efficient for the treatment of chronic pain or spontaneous on-going pain. In most cases, those active principles are only partially active and have important side effects which limit their use.

Benzodiazepines (BZDs) that are currently used for their anxiolytic or anticonvulsant properties are considered devoid of analgesic effect in human and their use in the treatment of acute or chronic pain is not recommended by current international guidelines (Corrigan et al., 2012, *Cochrane Database Syst Rev,* 5: p. CD009486; Wiffen et al., 2013, *Cochrane Database Syst Rev,* 11: p. CD01056). In human beings, research on the analgesic effect of BZDs is scarce and controversial. In healthy volunteers, classical BDZ site agonists such as clonazepam and clobazam exert weak analgesic effects when given at standard therapeutic doses (Besson et al., 2015, *Pain,* 156: 397-404).

In clinical research, diazepam has been used as an active placebo in a study seeking to demonstrate the analgesic effect of fentanyl in patients with chronic non-cancer neuropathic pain (Dellemijn et al., 1997, *Lancet,* 349:753-8). On the other hand, clonazepam is widely used in practice to treat neuropathic pain and has demonstrated efficacy in myofascial pain, temporomandibular joint dysfunction, cancer-related neuropathic pain and in stomatodynia when used topically (Gremeau-Richard et al., 2004, *Pain,* 108:51-7). However, the use of BZDs in chronic pain is rather limited by their side effects, such as sedation, memory impairment and dependence and most professionals skilled in the art of medical sciences have been convinced for the past 30 years that BZDs are not indicated for analgesia.

Specific pharmacological effects of BZD are thought to be associated with their degree of affinity for different subtypes of $GABA_A$ receptors found in the central nervous system. For instance, the anxiolytic and anticonvulsant properties of BZD are mainly mediated by the activation of the $\alpha 2$ and $\alpha 3$ subunits of the $GABA_A$ receptor while tolerance and sedation which remain major impediments to their use have been associated with the $\alpha 1$ subunit (Rudolph, 2011, *Nat Rev Drug Discov,* 10(9), 685-97).

Therefore, the main focus of the entire pharmacological BZD-oriented research was to try in the past twenty years to identify $\alpha 1$-sparing compounds.

The pharmaceutical industry was first interested in testing novel non-sedative anxiolytic compounds but following the discovery that enhancement of $\alpha 2$, $\alpha 3$ and possibly $\alpha 5$ $GABA_A$R-induced inhibition could revert pathological pain hypersensitivity in animal these compounds were also evaluated for their antihyperalgesic potential (Zeilhofer et al., 2012, supra; Dias et al., 2005, *J. Neurosci.,* 25(46), 10682-10688). However, despite a tremendous effort from the pharmaceutical industry, only a handful of these $\alpha 2/3$-selective compounds ever reached the clinical phases of development and all of them either showed excessive toxicity or lost their selectivity when used in human and caused unwanted sedation (Griebel et al., 2013, *Nat. Rev. Drug Discov.,* 12(9), 667-87). Further, many drug discovery and development programs have led to the development of BDZ site agonists with negligible activity at $\alpha 1 GABA_A$Rs such as L-838,417 (McKernan et al., 2000, *Nat Neurosci* 3, 587-592), TPA023 (Atack et al., 2006, *J Pharmacol Exp Ther.,* 316(1):410-2), and TPA023B (Atack et al., 2011, *J.Pharmacol. Exp. Ther.,* 316, 410-422) and other (Munro et al., 2009, *Trends Pharmacol. Sci.,* 30(9), 453-459). While the lack of activity at $\alpha 1 GABA_A$Rs avoids unwanted sedative and perhaps other undesired effects, those compounds were not pursued further either due to early toxicity or because they proved to be only partial agonists and the dose needed to reach substantial efficacy led to a loss in the benefit of their selectivity.

Recurrent failure in translating preclinical results into effectiveness in human explains why most research in this field has now been abandoned (Skolnick, 2012, *Trends Pharmacol. Sci.,* 33(11), 611-20). But still, there is a high need to find antihyperalgesic agents deprived from major side effects such as unwanted sedative effects.

Clobazam (CBZ) is a 1-5 BZD prescribed in all forms of anxiety and in epilepsy and commercialized under the name of Frisum™ or Onfi™ for the treatment of epilepsy and under the name of Urbanyl™ as antianxiolytic agent and as adjuvant treatment for epilepsy. It seems to exert less cognitive and psychomotor side effects compared with clonazepam and lorazepam. Clobazam is known to have higher binding affinity for $\alpha 2$ versus $\alpha 1$ receptor complexes, a difference which is shared by one of its metabolite N-desmethylclobazam, 8-Chloro-1-phenyl-1H-1,5-benzodiazepine-2,4(3H,5H)-dione), (NDMC or norclobazam) and which is not observed for example for clonazepam for which no distinction of affinity between $\alpha 2$ and $\alpha 1$ receptor complexes was observed. (Jensen et al., 2014, *PLOS ONE*, 9(2), e88456).

Therefore, there is a high need to find antihyperalgesic agents deprived from major side effects such as unwanted sedative effects.

SUMMARY OF THE INVENTION

The present invention relates to the unexpected finding that one of the metabolites of Clobazam, N-desmethylclobazam (NDMC), presents a clear combined selectivity targeting both the $\alpha 2$ and $\alpha 3$ subunits of the $GABA_A$ receptor as compared not only to other benzodiazepine such as diazepam but also as compared to its parent clobazam, which selectivity profile would be really beneficial for the treatment of chronic pain disorders as compared to existing antihyperalgesic agents and also as compared to its parent molecule clobazam.

Those findings are even more surprising that CBZ has shown rather weak analgesic is effects (Besson et al., 2015, supra) and a comparable selectivity for $\alpha 2$ over $\alpha 1$ receptors to the selectivity exhibited by NDMC (Jensen et al., 2014, *PLOS ONE*, 9(2), e88456). Additionally, the further unexpected long half-life of CBZ found in human (about 23-24 hours after a single oral dose of 20 or 30 mg of CBZ) could not lead to suspect that NDMC could have a reasonable contribution to the CBZ weak analgesic effects and even less that direct administration would lead to strong antihyperalgesic with an extremely broad therapeutic window offering the possibility of having an excellent therapeutic margin.

A first aspect of the invention provides N-desmethylclobazam and any formulation thereof for use in the prevention or treatment of a chronic pain disorder.

A second aspect of the invention relates to a use of N-desmethylclobazam for the preparation of a pharmaceutical formulation for the prevention or treatment of a chronic pain disorder.

A third aspect of the invention relates to a pharmaceutical formulation comprising N-desmethylclobazam combined with at least one antihyperalgesic agent, and at least one pharmaceutically acceptable carrier.

A fourth aspect relates to a method of preventing, treating or ameliorating a chronic pain disorder, said method comprising administering in a subject in need thereof a therapeutically effective amount of N-desmethylclobazam or a pharmaceutical formulation thereof, alone or in combination with at least one antihyperalgesic agent.

DESCRIPTION OF THE FIGURES

FIG. 7 shows the effects of NDMC in neuropathic pain model as described in Example 2 (thermal model). a: Paw withdrawal latencies (s, mean±SEM) in response to a defined radiant heat stimulus. Seven to 14 days after CCI surgery, NDMC 3, 10, 30 mg/kg and vehicle were given. Paw withdrawal latencies were measured before drug administration (baseline) and monitored for 24 hours after administration. Horizontal line indicates time interval used for the statistical analyses; b: Maximal possible effect (%) in paw withdrawal latency following administration of 3, 10, 30 mg/kg of NDMC as compared to vehicle in wild-type mice. Black circles, individual mice; lines mean±SEM; * $P<0.001$,  $P<0.01$, * $P<0.05$ significant versus vehicle-treated mice; ANOVA followed by Dunnett's post hoc test; F(3,49)=15.2, n=14, 13, 13, 12 for vehicle and 3, 10 and 30 mg kg$^{-1}$ NDMC.

FIG. 8 shows the effects of NDMC in neuropathic pain model as described in Example 2 (mechanical model). a: Paw withdrawal thresholds (g, mean±SEM) in response to mechanical stimulation with dynamic von Frey filaments. Seven to 14 days after CCI surgery, NDMC 3, 10, 30 mg/kg and vehicle (veh.) were given. Paw withdrawal thresholds were measured before drug administration (baseline) and monitored for 24 hours after administration.. Horizontal line indicates time interval used for the statistical analyses; b: Maximal possible effect (%) in paw withdrawal threshold following administration of 3, 10, 30 mg/kg of NDMC as compared to vehicle in wild-type mice. Black circles, individual mice; lines mean±SEM; * P<0.001,  P<0.01, * P<0.05 significant versus vehicle-treated mice, ANOVA followed by Dunnett's post hoc test, F(3,41)=19.8, n=10, 12, 11, 11 for vehicle and 3, 10 and 30 mg kg-1 NDMC, respectively.

DETAILED DESCRIPTION

The term "chronic pain disorder" includes neuropathic pain, fibromyalgia, somatoform pain disorder, pain related to chronic fatigue syndrome, endometriosis, inflammatory is bowel disease, visceral pain, interstitial cystitis, temporomandibular joint dysfunction, and vulvodynia. According to a particular aspect, such disorder includes those described in *Chronic Pain: New Insights for the Healthcare Professional*: 2013, *Scholarly Editions*.

The term "neuropathic pain" as defined relates to pain resulting from a condition related to peripheral or central nervous system injury or dysfunction or infectious diseases.

According to a particular embodiment, neuropathic pain includes pain resulting from an infectious disease such as herpes, such as herpes zoster or HIV infections such as HIV polyneuropathy.

According to another particular embodiment, neuropathic pain includes pain resulting from traumatic nerve injury such as spinal cord injury, sciatica, root avulsions, painful traumatic mononeuropathy, phantom limb pain, postsurgical pain syndromes (e.g., postmastectomy syndrome, post-thoracotomy syndrome, phantom pain), complex regional pain syndrome (reflex sympathetic dystrophy and causalgia), stump/neuroma pain, post-ischemic pain (stroke), fibromyalgia, reflex sympathetic dystrophy (RSD), vertebral disk rupture.

According to another particular embodiment, neuropathic pain includes pain resulting from metabolic or ischemic injuries such as diabetic neuropathy.

According to another particular embodiment, neuropathic pain includes pain resulting from central pain syndromes (potentially caused by virtually any lesion at any level of the nervous system), such as stroke, post-ischemia, trigeminal neuralgia, multiple sclerosis and/or lateral amyotrophic sclerosis.

According to another particular embodiment, neuropathic pain includes pain resulting from drug-induced neuropathic pain, such as cancer chemotherapeutic-induced neuropathic pain.

According to another particular embodiment the term "neuropathic pain" includes pain associated with a condition selected from the group consisting of herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, and cancer chemotherapeutic-induced neuropathic pain such as postherpetic neuralgia, root avulsions, painful traumatic mononeuropathy, painful polyneuropathy (particularly due to diabetes), central pain syndromes (potentially is caused by virtually any lesion at any level of the nervous system), postsurgical pain syndromes (e.g., postmastectomy syndrome, post-thoracotomy syndrome, phantom pain), complex regional pain syndrome (reflex sympathetic dystrophy and causalgia), stump/neuroma pain, post-ischemic pain (stroke), fibromyalgia, reflex sympathetic dystrophy (RSD), vertebral disk rupture and/or trigeminal neuralgia.

The term "antihyperalgesic agent" as referred to herein, includes agents which are known for their anti-hyperalgesic properties and/or for their binding selectivity to the α2 and/or α3 subunits of the GABA$_A$ receptor as compared to the α1 subunit of the GABA$_A$ receptor.

Other useful forms of antihyperalgesic agents in the context of the invention include other pharmaceutically acceptable active salts of said compounds, as well as active isomers, enantiomers, polymorphs, solvates, hydrates, and/or prodrugs of said compounds.

The term "pharmaceutically acceptable" refers to a carrier comprised of a material that is not biologically or otherwise undesirable.

The term "carrier" refers to any component present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions such as improvement or remediation of damage.

In particular, treatment of chronic pain disorders comprises to normalize or decrease the level or intensity of felt pain and/or the length of the pain episodes and/or to improve is the quality of life.

The term "subject" as used herein refers to mammals. For examples, mammals contemplated by the present invention include human, primates, domesticated animals such as cattle, sheep, pigs, horses, laboratory rodents and the like.

The term "efficacy" of a treatment according to the invention can be measured based on changes in the course of disease in response to a use according to the invention. For example, the efficacy of a treatment according to the invention can be measured by a change of pain intensity on a visual analog scale, by Patient Global Impression of Change (PGIC) scores. For another example, the efficacy of the treatment of the invention might be assessed through the measurement of a reduced occurrence and/or length of pain episodes.

Compositions

The invention provides pharmaceutical or therapeutic agents as compositions and methods for treating a subject, preferably a mammalian patient, and most preferably a human patient who is suffering from a medical disorder, and in particular a chronic pain disorder.

In a particular embodiment, the invention provides a pharmaceutical formulation according to the invention for use as a medicament.

According to a particular embodiment, the pharmaceutical composition according to the invention comprises N-desmethylclobazam and any pharmaceutically acceptable salt thereof.

Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient may be placed into the form of pharmaceutical compositions and may be employed as solids, such as tablets or filled capsules, or liquids such as solutions, suspensions, ointments, emulsions, elixirs, or capsules filled with the same, films or gels, all for oral use. The compositions may also be formulated as a dry product for reconstitution with water or other suitable vehicle before use.

Compositions of this invention as liquid formulations including, but not limited to, aqueous or oily suspensions, solutions, emulsions, syrups, and elixirs.

Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®. Further materials as well as formulation processing techniques and the like are set out in The Science and Practice of Pharmacy (Remington: The Science & Practice of Pharmacy), $22^{nd}$ Edition, 2012, Lloyd, Ed. Allen, Pharmaceutical Press, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycolate. Wetting agents include, but are not limited to, sodium lauryl sulfate. Tablets may be coated according to methods well known in the art.

Mode of Administration

Compositions of this invention may be administered in any manner by oral route including to the mucosal surfaces of the oral cavity including the gingiva, the floor of the oral cavity, cheeks, lips, tongue, teeth.

Combination

According to the invention, N-desmethylclobazam or any suitable pharmaceutically acceptable thereof and pharmaceutical formulations thereof may be administered alone or in combination with at least one anti-hyperalgesic agent.

According to a particular aspect, anti-hyperalgesic co-agents according to the invention is include N-methyl D-aspartate (NMDA) antagonists such as ketamine, methadone, memantine, amantadine and dextromethorphan or those described in Suzuki et al., 2009, Curr. Opin. Anaesthesiol., 22(5), 618-22.

The invention encompasses the administration of N-desmethylclobazam and pharmaceutical formulations thereof to an individual simultaneously or sequentially with at least a co-agent useful in the treatment of hyperalgesia and/or chronic pain disorders (e.g. multiple drug regimens). N-desmethylclobazam or a pharmaceutical formulation thereof that is administered simultaneously with said co-agent can be administered in the same or different composition(s) and by the same or different route(s) of administration.

According to a particular aspect, NDMC is to be administered at a dose suitable to achieve a plasma concentration in human of about 100-2' 500 ng/ml.

According to another particular aspect, NDMC is to be administered at a daily dose of about 5 to about 40 mg, for example from about 5 to about 20 mg or from about 10 to about 40 mg.

According to another particular aspect, NDMC is to be administered at a daily dose of about 0.07 to about 0.8 $mg/kg^{-1}$.

In a particular embodiment, dosages used for administration of N-desmethylclobazam or any suitable pharmaceutically acceptable thereof include, but are not limited to, an effective amount within the dosage range of about 10 to about 120 mg. The dosage range may vary depending on the circumstances of each case, the underlying disease, the clinical indication and the desired intensity of pain relief which is aimed at and/or necessary.

According to one embodiment, is provided a pharmaceutical formulation comprising—N-desmethylclobazam or any suitable pharmaceutically acceptable thereof combined with at least one anti-hyperalgesic agent, and at least one pharmaceutically acceptable carrier.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

In a particular embodiment, combined use or formulations might be further combined with at least one anti-hyperalgesic agent, in particular at least one N-methyl D-aspartate (NMDA) antagonist.

Patients

In an embodiment, patients according to the invention are patients suffering or at risk of suffering from chronic pain disorders.

In a further embodiment, patients according to the invention are patients suffering or at risk of suffering from neuropathic pain.

In a further embodiment, patients according to the invention are patients suffering or at risk of suffering from fibromyalgia.

Use According to the Invention

In another embodiment of the invention is provided a use of N-desmethylclobazam or any suitable pharmaceutically acceptable thereof alone in combination with at least one anti-hyperalgesic agent for the preparation of a pharmaceutical formulation for the prevention or treatment of a chronic pain disorder.

In another embodiment of the invention is provided a use of N-desmethylclobazam or any suitable pharmaceutically acceptable thereof for the prevention or treatment of a chronic pain disorder, wherein said N-desmethylclobazam or any suitable pharmaceutically acceptable thereof is to be used alone or in combination with at least one anti-hyperalgesic agent.

In another embodiment, the invention provides a method of prevention and/or treatment of a chronic pain disorder comprising the administration of a therapeutically effective amount of N-desmethylclobazam or any suitable pharmaceutically acceptable thereof of a pharmaceutical formulation thereof, alone or in combination with at least one anti-agent in a mammal in need thereof.

In another embodiment, is provided a compound, a use or a method according to the invention, wherein the disorder is a neuropathic pain disorder.

In another embodiment, is provided a compound, a use or a method according to the invention, wherein the disorder is fibromyalgia.

Uses, methods and compositions according to the invention may be useful in the prevention, repression or treatment of chronic pain disorders.

Examples illustrating the invention will be described hereinafter in a more detailed manner and by reference to the embodiments represented in the Figures.

EXAMPLES

The following abbreviations refer respectively to the definitions below:

BZD (benzodiazepines); C (concentration); CBZ (clobazam); DZP (diazepam); GABA (γ-aminobutyric acid); $GABA_A$ receptor or $GABA_AR$ (ionotropic receptor and ligand (GABA)-gated ion channel); I (current intentity); NDMC (N-desmethylclobazam).

Example 1: Selectivity

Selectivity of N-desmethylclobazam for both α2 and α3 subunits of $GABA_A$ recombinant receptor as compared to affinity for α1/5 subunits is measured by standard electrophysiology measurements as compared other benzodiazepines and also as compared to its parent clobazam.

Drugs

DZP and CBZ were obtained from Lipomed AG, Arlesheim, Switzerland. NDMC was obtained from Imaginechem Co, Ltd, Hangzhou, China. NDMC was tested for purity, which was 99%.

Electrophysiology

The effects of DZP, CBZ and NDMC on currents mediated through recombinant $GABA_ARs$ were studied in HEK293 cells (ATCC) transiently transfected with rat $GABA_AR$ subunits using lipofectamine LTX 46 (Invitrogen). To ensure expression of the γ2 subunit (required for modulation of $GABA_AR$ currents by BDZs) in all recorded cells, cells were transfected with a plasmid expressing the γ2 subunit plus eGFP from an IRES (internal ribosome entry site) and only eGFP-positive cells were selected for recordings. The transfection mixture contained (in μg): 1 βx, 1 βy, 3 γ2/eGFP (used as a marker of successful transfection). Whole-cell patch-clamp recordings were made 18-36 hrs after transfection at room temperature (20-24° C.) and at a holding membrane potential of −60 mV. Recording electrodes were filled with solution containing (in mM): 120 CsCl, 10 EGTA (aminopolycarboxylic acid), 10 HEPES (4-(2-hydroxyethyl)-1-piperazineethanesulfonic acid, pH 7.40), 4 MgCl2, 0.5 GTP (guanosine-5'-triphosphate) and 2 ATP (adenosine triphosphate). The external solution contained (in mM): 150 NaCl, 10 KCl, 2.0 $CaCl_2$, 1.0 $MgCl_2$, 10 HEPES (pH 7.40), and 10 glucose. GABA was applied to the recorded cell using a manually controlled pulse (6-10 s) of a low sub-saturating GABA concentration ($EC_{10}$). $EC_{10}$ values of GABA were 1 μM, 5 μM, 8 μM, and 1 μM for the four $GABA_AR$ combinations (α1β2γ2, α2β3γ2, α3β3γ2 and α5β2γ2), respectively. $EC_{50}$ values and Hill coefficients ($n_H$) were obtained from fits of normalized concentration-response curves to the equation:

$$I_{GABA} = I_{max}[GABA]^{n_H}/([GABA]^{n_H} + [EC_{50}]^{n_H}).$$

$I_{max}$ was determined as the average maximal current elicited by saturating concentration of GABA (30 μM–3 mM, depending on the subunit composition). DZP, CBZ and NDMC were dissolved in DMSO (dimethyl sulfoxide, final concentration<0.1%) and subsequently diluted on the day of the experiment in external solution and were co-applied with GABA without pre-incubation. Concentration-response curves were fitted using the equation for sigmoidal concentration-response curve with variable slope:

$$E(C) = E_{max} \cdot [C] \cdot n_H / ([C]^{n_H} + [EC_{50}] \cdot n_H)$$

Figure 4:
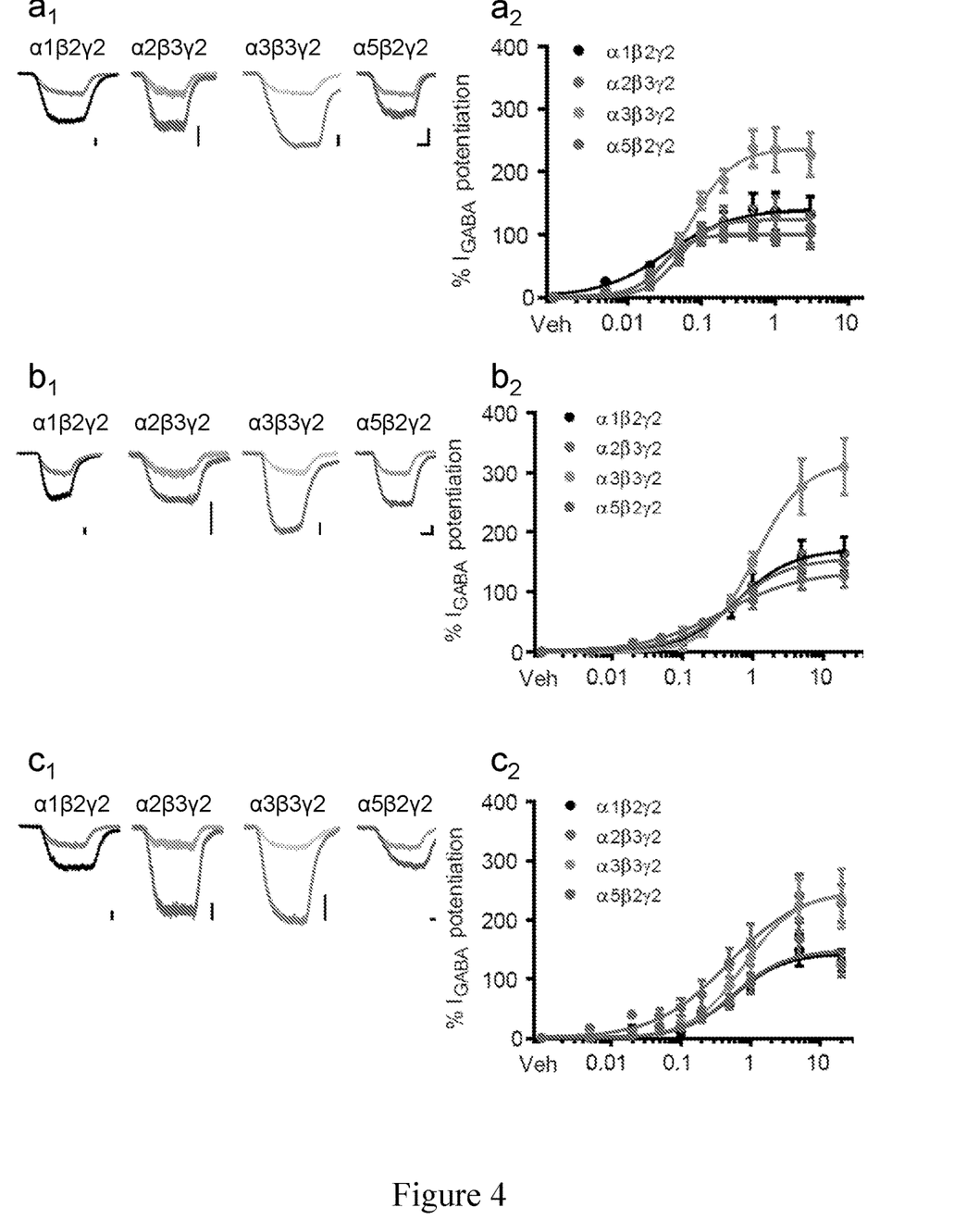
FIG. 4 shows $\alpha 1\beta 2\gamma 2$, $\alpha 2\beta 3\gamma 2$, $\alpha 3\beta 3\gamma 2$ and $\alpha 5\beta 2\gamma 2$ $GABA_A$Rs-mediated currents upon DZP ($a_{1,2}$), CBZ (1,2) and NDMC ($c_{1,2}$) application. $a_1$, $b_1$, $c_1$: show GABA-evoked membrane currents in control conditions (light traces) and upon compounds application (dark traces). Saturating concentration of 1 µM DZP ($a_1$), 20 µM CBZ ($b_1$), or 20 µM NDMC ($c_1$), were applied. Scale bars: 2 s and 200 pA. Concentration response curves upon application of DZP ($a_2$), CBZ ($b_2$) and NDMC ($c_2$) obtained for the four $GABA_A$R subtypes at $EC_{10}$ of GABA. Data are shown as mean±SEM. Curves represent fits to Hill's equation with a baseline fixed to 0 n=5-7 for all data points.
Figure 5:
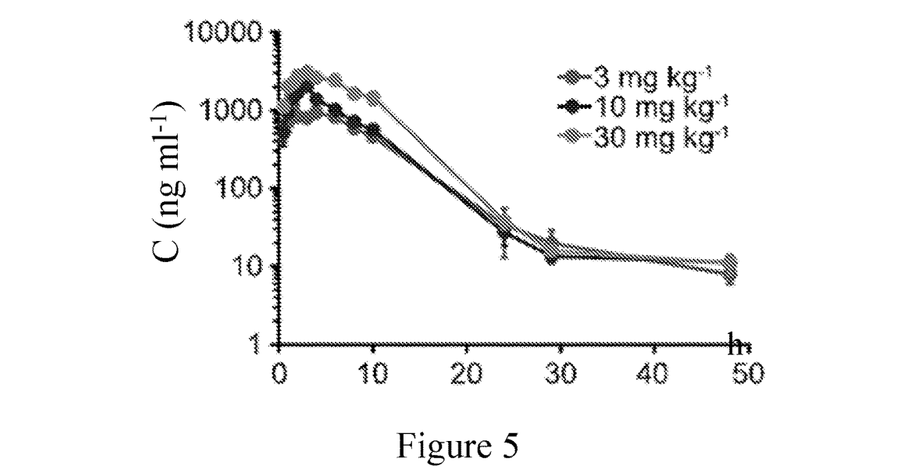
FIG. 5 shows NDMC whole blood concentrations (mean±SEM) over time after NDMC p.o. administration (n=3 per group).

DZP, CBZ and NDMC potentiated currents mediated through α1β2γ2, α2β3γ2, α3β3γ2 and α5β2γ2 $GABA_ARs$ (abbreviated herein α1-, α2-, α3- and α5$GABA_ARs$ respectively) but did not directly activate $GABA_AR$ currents at the concentrations tested (up to 3 μM for DZP, and up to 20 μM for CBZ and NDMC) (FIG. 4). DZP potentiated currents mediated through all four receptor subtypes with $EC_{50}$ values between 0.029 and 0.071 μM. Potentiation of currents by DZP was strongest for α3$GABA_ARs$ (237% increase upon DZP application), while potentiation of the other three α1-, α2-, and α5-$GABA_ARs$ subtypes ranged between 100% and 141% upon DZP application (FIG. 4a). At sub-saturating DZP concentrations (<$EC_{50}$, which are probably more relevant to therapeutic effects, FIG. 4a2) α1$GABA_AR$ mediated currents were potentiated more strongly than α2-, α3- and α5-$GABA_ARs$ mediated currents. CBZ and NDMC were less potent than DZP with $EC_{50}$ values between 0.40 and 1.1 μM and between 0.49 and 0.81 μM, respectively (FIG. 4b, c). Potentiation of currents by CBZ was strongest for α3$GABA_ARs$ (about 300% increase upon CBZ application), while potentiation of the other three α1-, α2-, and α5-$GABA_ARs$ subtypes was about 150% upon DZP application (FIG. 4b). At sub-saturating CBZ concentrations (<$EC_{50}$, FIG. 4b2) α1$GABA_AR$ mediated currents were potentiated similarly to α2-, α3- and α5-$GABA_ARs$ mediated currents. Potentiation of currents by NDMC was strongest for α2- and α3-$GABA_ARs$ (253% and 245% increase upon NDMC application) and considerably lower for α1- and α5-$GABA_ARs$ (143% and 148% increase upon NDMC application, FIG. 4c). NDMC had the most favorable α2/α1GABA$_A$R selectivity ratio. However, unexpectedly and more importantly at sub-saturating concentrations, NDMC potentiation effect was highest for α2- followed by α3-, and lowest for α5- and α1-GABA$_A$Rs mediated currents (FIGS. 4c2 & 5).

Therefore, those electrophysiology measurements show a clear separation between the current concentration-response curves for GABA potentiation (%) of α1/5 and α2/3 recombinant GABA$_A$ receptors for N-desmethylclobazam and show pronounced differences between compounds not only with respect to their selectivity but more importantly, in their efficacy of potentiation on GABA$_A$R subtypes. Saturating concentrations DZP and CBZ, namely 1 μM and 20 μM potentiated both GABA$_A$R subtypes with similar efficacy, while NDMC clearly favored α2- over α1GABA$_A$Rs. At low concentrations (<EC$_{50}$), remarkably, NDMC preferred α2GABA$_A$Rs across the entire concentration range tested, while CBZ had about similar effects on α2- and α1GABA$_A$Rs and DZP favored α1GABA$_A$Rs. Those data support the unexpected and advantageous pharmacological profile of NMDC.

Example 2: Effect of N-desmethylclobazam on anti-antihyperalgesia in Mice

The effects of N-desmethylclobazam (NMDC) were tested in different models of hyperalgesia in wild type mice all having the same genetic background as follows.

Mice

Experiments were performed in wild-type mice (genetic background C57BL/6J or 129X1/SvJ), and in homozygous triple and quadruple (H→R) GABA$_A$R point-mutated mice of the 129X1/SvJ background (Ralvenius et al., 2015, supra). Quadruple point-mutated mice were generated by cross breeding of single point-mutated mice (Crestani et al., 2002, *PNAS*, 99(13): 8980-8985; Low et al., 2000, *Science* 290(5489): 131-134; Rudolph et al., 1999, *Nature*, 401 (6755): 796-800). Quadruple point mutated mice carry the H→R mutation in the α1, α2, α3, and α5 subunits that is in all α subunits that can form a high affinity BDZ binding site.

Neuropathic Pain Model

A chronic constriction injury (CCI) model was used. Unilateral constriction injury of the left sciatic nerve just proximal to the trifurcation was performed. Anesthesia was induced and maintained by 2% isoflurane, combined with oxygen (30%). The sciatic nerve was exposed at the mid-thigh level proximal to the sciatic trifurcation by blunt dissection through the biceps femoris muscle. 5±7 mm of nerve were freed of adhering tissue and three chromic gut ligatures (4/0) (Ethicon) were loosely put around the nerve with about 1 mm spacing. The ligatures were tied until they elicited a brief twitch in the hindlimb. The surgical wound was closed in layers. Heat hyperalgesia and mechanical sensitization were assessed 7 days after surgery.

Heat Hyperalgesia

Figure 1:
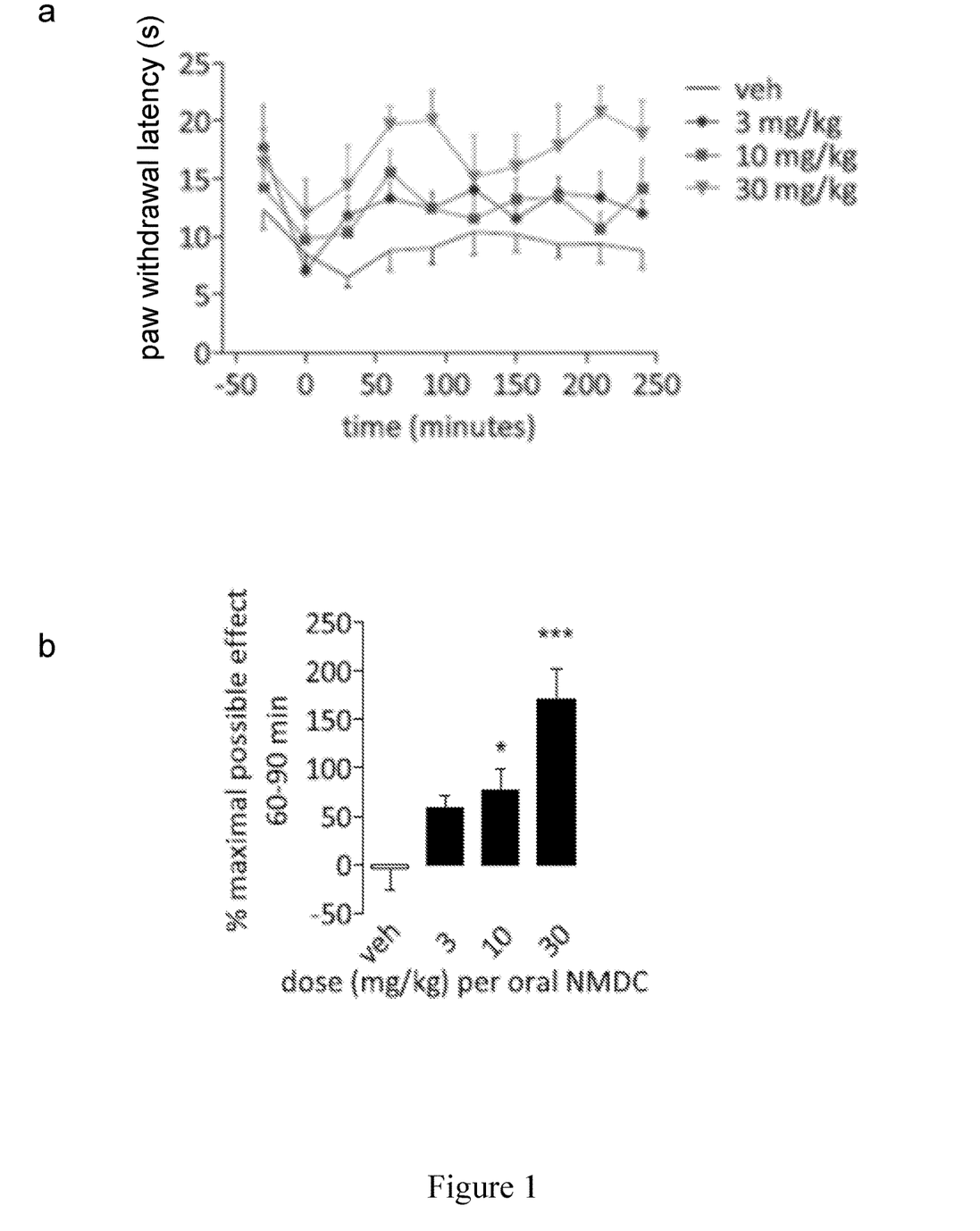
FIG. 1 shows the effects of NDMC in neuropathic pain model as described in Example 2 (thermal model). a: Paw withdrawal latencies (s, mean±SEM) in response to a defined radiant heat stimulus. On day 7 after CCI surgery, NDMC 3, 10, 30 mg/kg and vehicle were given. Paw withdrawal latencies were measured before drug administration (baseline) and monitored for 4 hours after administration. (n=10 per dose); b: Maximal possible effect (%) in paw withdrawal latency following administration of 3, 10, 30 mg/kg of NDMC as compared to vehicle in wild-type mice. (n=10 per dose).
Figure 7:
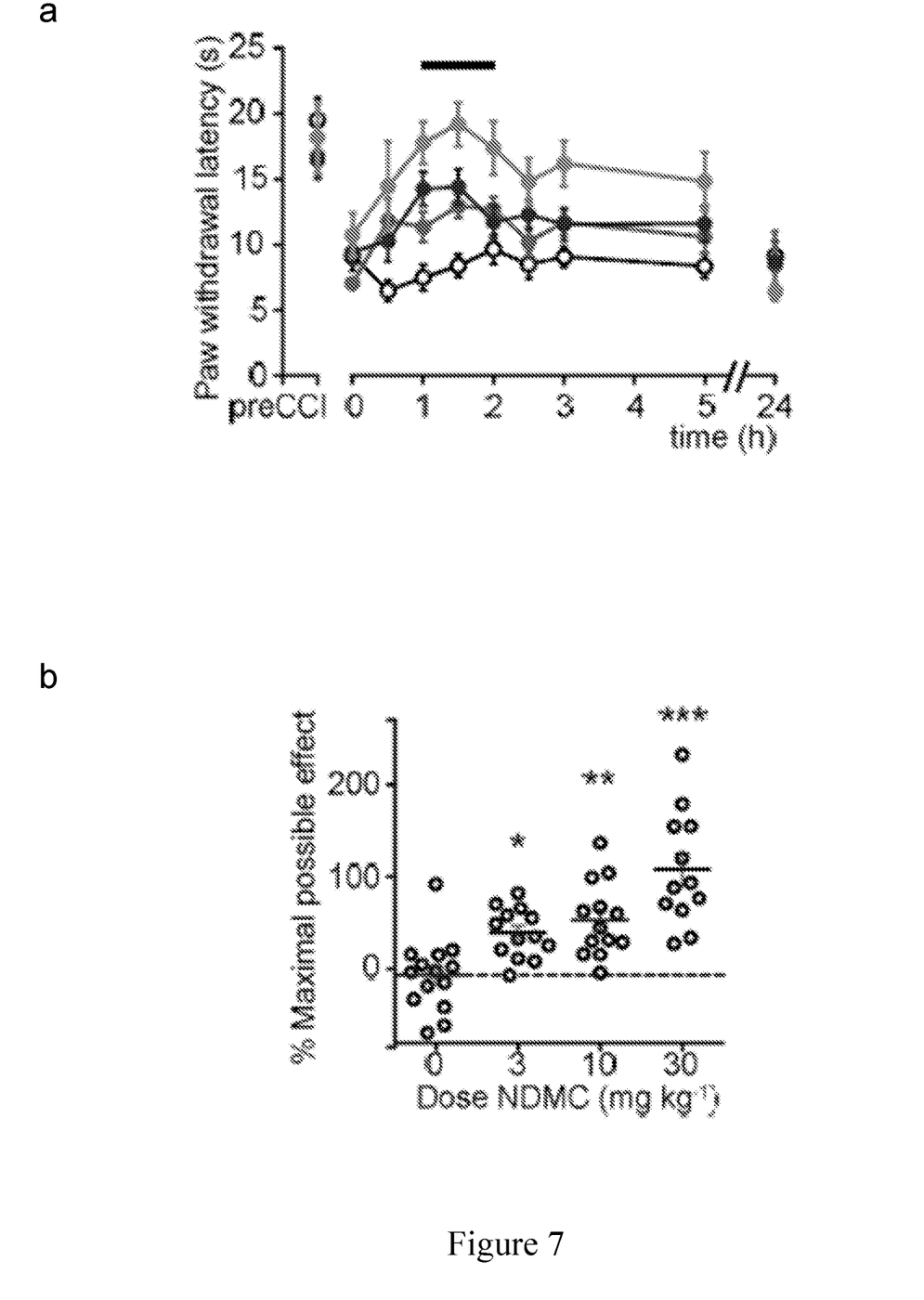

Paw withdrawal latencies upon exposure to a defined radiant heat stimulus were measured using a commercially available apparatus (Plantar Test, Ugo Basile, Comerio, Italy). Four to five measurements were taken in each animal for every time point and averaged. Measurements of paw withdrawal latencies of injured paw and of the contralateral paw were made alternately. Results related to the injured paw in C57BL/6J mice are shown in FIG. 1 (a, b) and FIG. 7 (a, b). After chronic constriction of the sciatic nerve (CCI), paw withdrawal latencies fall from 15 to 5 secondes (thermal hypersensitivity). NDMC dose-dependently reversed this hypersensitivity. Similar results were obtained in mice of the 129X1/SvJ background. In the quadruple point-mutated mice NDMC (30 mg kg$^{-1}$) had completely lost its antihyperalgesic effects.

Mechanical Hyperalgesia

Figure 2:
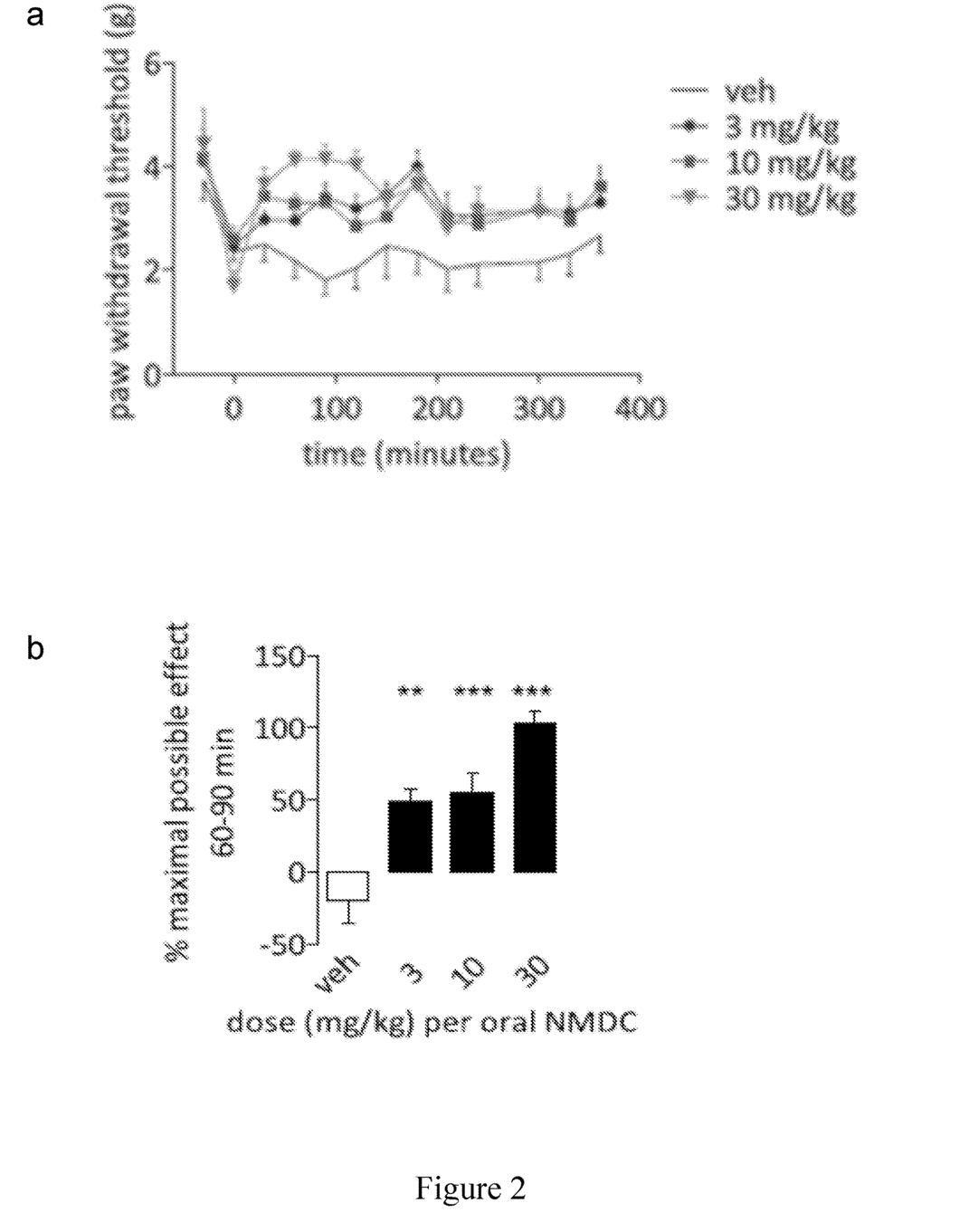
FIG. 2 shows the effects of NDMC in neuropathic pain model as described in is Example 2 (mechanical model). a: Paw withdrawal thresholds (g, mean±SEM) in response to mechanical stimulation with dynamic von Frey filaments. On day 7 after CCI surgery, NDMC 3, 10, 30 mg/kg and vehicle (veh.) were given. Paw withdrawal thresholds were measured before drug administration (baseline) and monitored for 6 hours after administration. (n=10 mice per doses); b: Maximal possible effect (%) in paw withdrawal threshold following administration of 3, 10, 30 mg/kg of NDMC as compared to vehicle in wild-type mice. (n=10 mice per doses).
Figure 8:
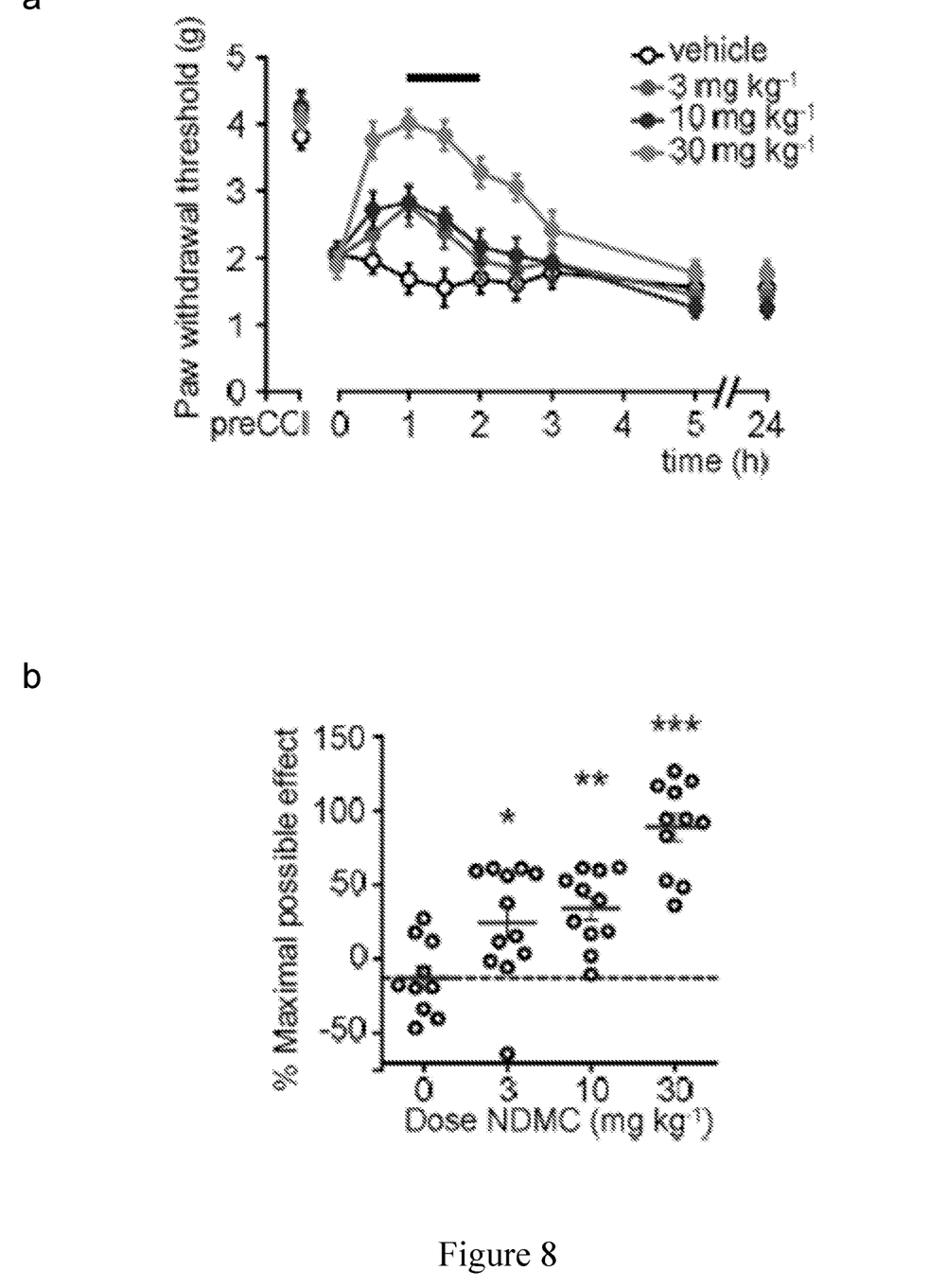

Mechanical sensitivity was assessed with dynamic von Frey filaments (IITC, Woodland Hills, Calif.). 4-5 measurements were made for each time point and animal and averaged. Measurements of paw withdrawal thresholds of the injured paw and of the contralateral paw were made alternately. Results related to the injured paw in C57BL/6J mice are shown in FIG. 2 (a, b) and FIG. 8 (a, b). After chronic constriction of the sciatic nerve (CCI), paw withdrawal threshold fall from 4 to 2 grams (mechanical hypersensitivity). NDMC dose-dependently reversed this hypersensitivity as compared is to vehicle group (veh.). Similar results were obtained in mice of the 129X1/SvJ background. In the quadruple point-mutated mice NDMC (30 mg kg$^{-1}$) had completely lost its antihyperalgesic effects.

Example 3: Absence of Detectable Sedation Effect of N-desmethylclobazam

Figure 3:
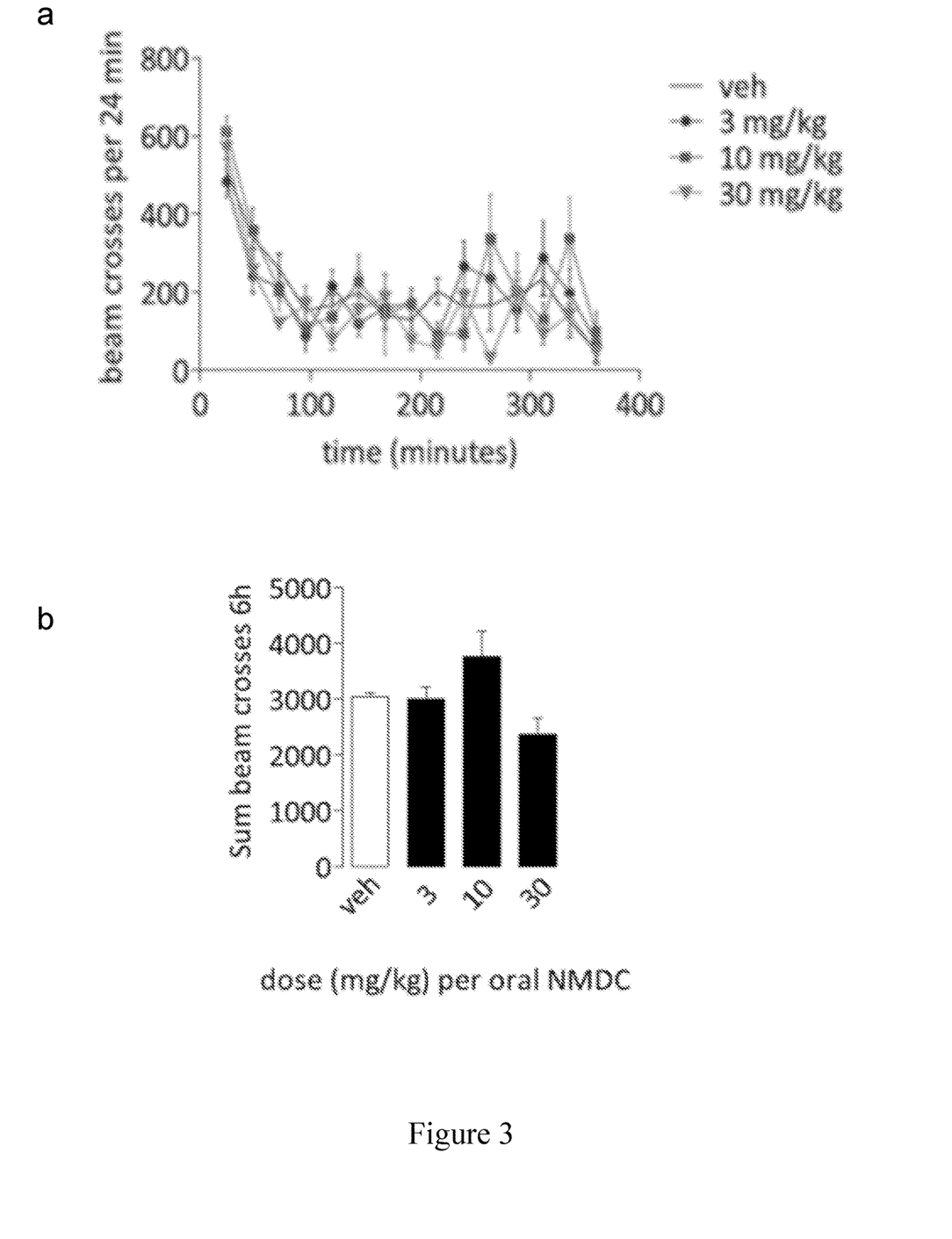
FIG. 3 shows the results on motor activity as described in Example 3; a: Motor activity expressed as the total number of beam crossed (n=6 per doses); b: Maximal possible effect (%) on motor activity after administration of 3, 10, 30 mg/kg of NDMC as compared to vehicle (veh.) in wild-type mice. (n=6 per doses).
Figure 9:
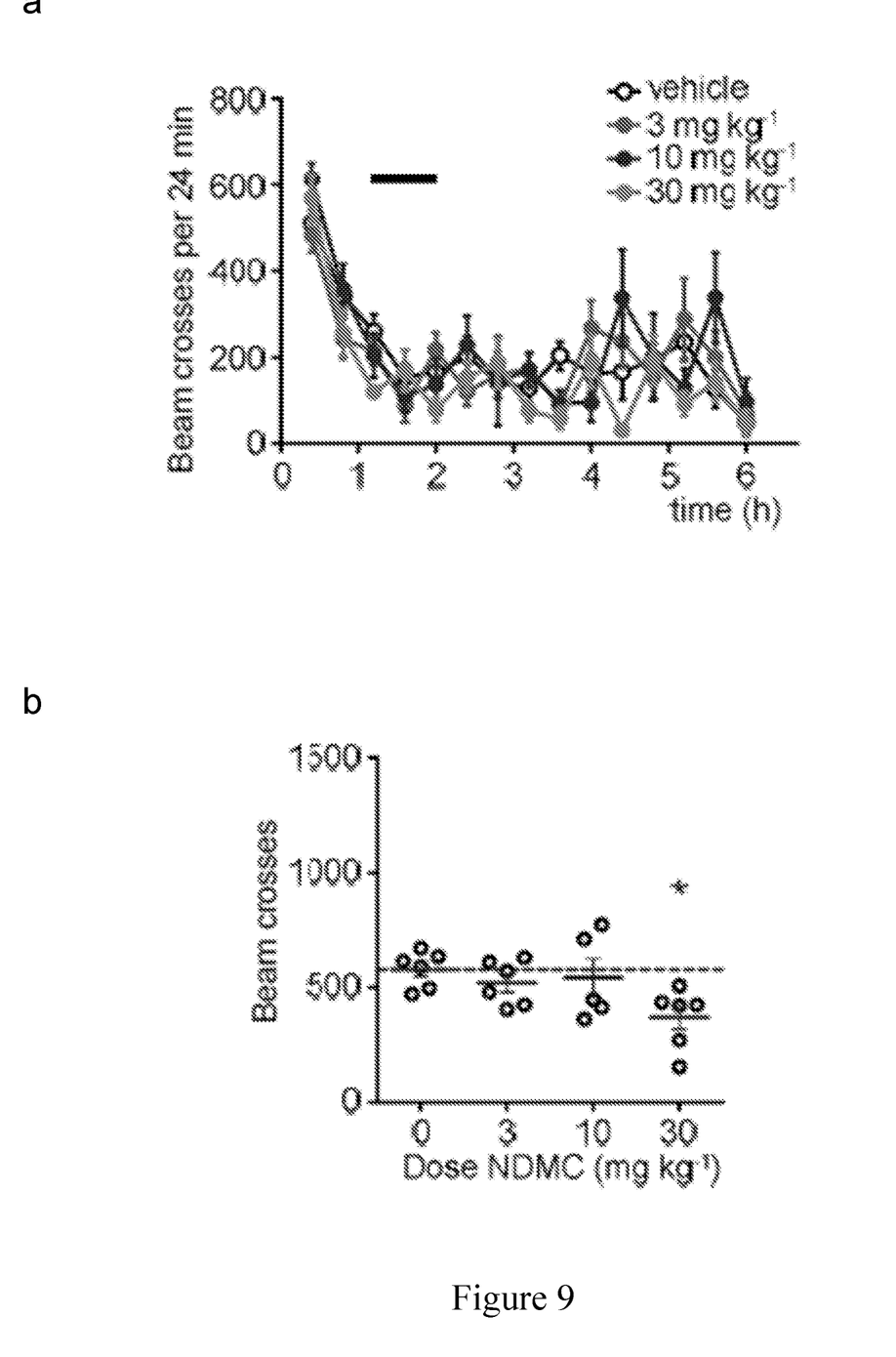
FIG. 9 shows the results on motor activity as described in Example 3; a: Motor activity expressed as the total number of beam crossed. Horizontal line indicates time interval used for the statistical analyses; b: Maximal possible effect (%) on motor activity after administration of 3, 10, 30 mg/kg of NDMC as compared to vehicle (veh.) in wild-type mice. Black circles represent individual mice, lines indicate mean±SEM, dashed lines show vehicle group average. * P<0.05 significant versus vehicle-treated mice, ANOVA followed by Dunnett's post hoc test, F(3,19)=3.2, n=6, 6, 5 and 6 for vehicle and NDMC 3, 10 and 30 mg kg$^{-1}$.

Mice (C57BL/6J or 129X1/SvJ) were tested during the light phase of the day-night cycle. After NDMC 3,10,30 mg/kg or vehicle, mice (n=6 per dose) were placed in individual circular enclosures (diameter 20 cm), equipped with 4 photocells. Motor activity expressed as the total number of photocell interruptions was recorded for 6 h. Results obtained for C57BL/6J are shown in FIG. 3 and FIG. 9 and support that NDMC did not impair motor activity at any dose. In 129X1/SvJ mice NDMC did not cause any measurable reduction in locomotor activity at any of tested doses.

Altogether these data show that N-desmethylclobazam present a clear an unexpected dual selectivity for both the α2 and α3 subunits of the GABA$_A$ receptor as compared to α1 and α5 subunits. This selectivity profile together with the neuropathic pain model data supports the usefulness of N-desmethylclobazam and its pharmaceutically acceptable salts in the prevention and/or treatment of chronic pain disorders. Further, such a dual selectivity offers a clear advantage in terms of therapeutic index over the existing antihyperalgesic agents and also as compared to the administration of its parent molecule clobazam.

Example 4: Pharmacokinetic Parameters of NDMC

Pharmacokinetic parameters of NDMC following oral administration in C57BL/6 mice were determined and allowed to test whether antihyperalgesia after NDMC administration was mediated by NDMC itself and not by a down-stream metabolite.

NDMC Pharmacokinetics

Pharmacokinetic properties of NDMC were evaluated using the dried blood spot sampling method. This technique allows collecting multiple bleeds from the same animal over a large time window (Deglon et al., 2011, *Pharm. Biomed. Analysis*, 54(2): 359-367). Four μl of whole blood were collected and spotted onto a filter paper card from Whatman (Dassel, Germany) at different time points between 0 and 48 h after NDMC administration. NDMC concentration measurements were performed using a fully validated LCMS-MS (liquid chromatography—mass spectrometry or HPLC) method. Pharmacokinetic parameters were estimated by a noncompartmental method using WinNonlin® version 5.2 (Pharsight, Mountainview, Calif., USA).

Blood NDMC concentrations were measured with HPLC following single oral doses of 3, 10 and 30 mg kg$^{-1}$ in three mice per group (FIG. 5). Maximal blood levels of NDMC were reached within 2-3 hrs. Average maximum plasma concentrations of NDMC were reached after about 2.5 hrs and were 1.2, 1.9, and 3.3 µg ml$^{-1}$ and plasma half-life was between 4.6 and 5.6 hrs (Table 1).

TABLE 1

| NDMC dose (mg/kg) | Half-life (h; ± SD) | $C_{max}$ (µg/ml) | AUC (h* µg/ml) | $T_{max}$ (h) |
|---|---|---|---|---|
| 3 | 5.6 ± 0.6 | 1.19 ± 2.53 | 11.15 ± 1.66 | 2.0 ± 0.9 |
| 10 | 4.6 ± 1.6 | 1.91 ± 1.34 | 14.72 ± 4.38 | 3.0 ± 0.0 |
| 30 | 4.7 ± 0.3 | 3.31 ± 1.01 | 32.28 ± 5.09 | 2.7 ± 0.6 |

These data correlate well with the time course of antihyperalgesia following NDMC administration confirming that NDMC did not require further metabolism for its antihyperalgesic action.

Example 5: Therapeutic Window of NDMC

One of the major reasons limiting the clinical use of DZP and other non-selective BDZ for pain therapy is the dose-limiting sedation that already occurs at doses much lower than those necessary for antihyperalgesia and therefore, classical BDZ hence lack a therapeutic window for antihyperalgesia (Ralvenius et al., 2015, supra). Therefore, evaluation of the possible therapeutic window of NDMC was carried out as follows. Triple and single point-mutated mice were generated as described in Example 2 Hyperalgesia assessed as in Example 2 and sedation assessed as in Example 3.

Figure 6:
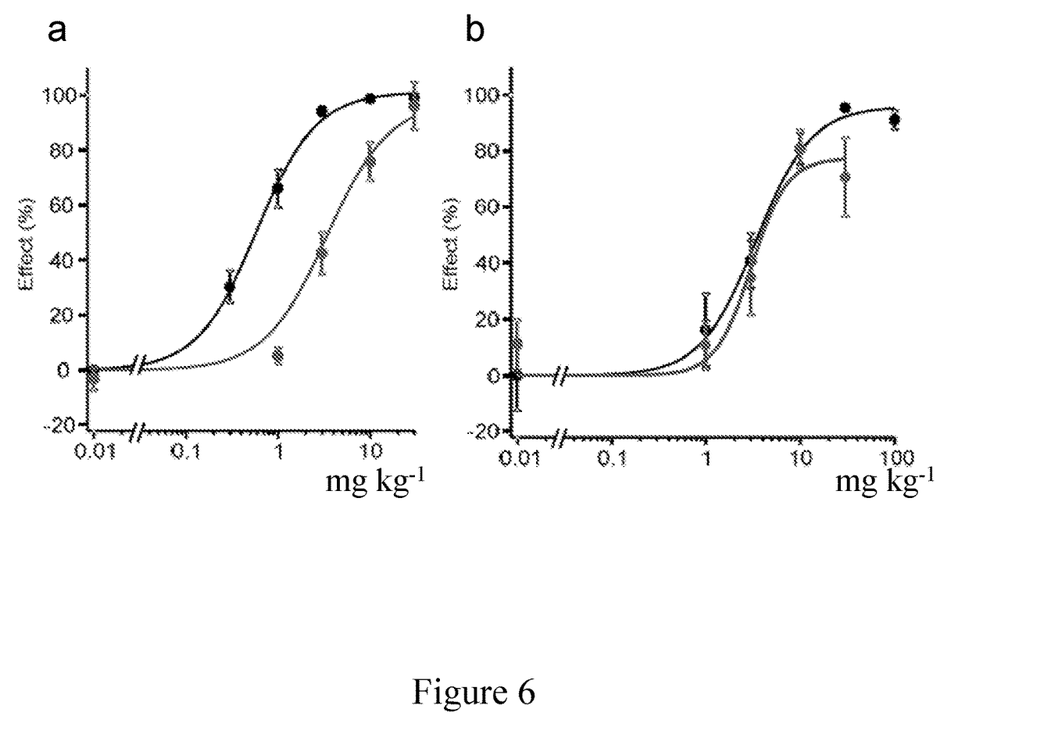
FIG. 6 shows dose-dependence of sedative ($\alpha 1 GABA_AR$-mediated) and antihyperalgesic ($\alpha 2 GABA_AR$-mediated) actions of DZP (a) and NDMC (b). a) Sedation (black dots): n=6, 6, 8, 5 and 5 for vehicle and DZP 1, 3, 10 and 30 mg $kg^{-1}$, respectively. Antihyperalgesia (grey dots): n=7, 7, 7, 6 and 6, for vehicle and DZP 1, 3, 10 and 30 mg $kg^{-1}$, respectively. (b) Sedation (black dots): n=10, 5, 5, 5, 5 and 4 for vehicle and NDMC 1, 3, 10, 30 and 100 mg $kg^{-1}$, respectively. Antihyperalgesia grey dots): n=6, 6, 6, 5 and 5 mice, for vehicle and NDMC 1, 3, 10 and 30 mg $kg^{-1}$, respectively. Data points are shown as mean±SEM.

The dose dependencies of DZP- and NDMC-induced sedation and antihyperalgesia were compared (FIG. 6). To avoid confounding effects of anxiolysis in sedation experiments, and of sedation on antihyperalgesia experiments triple point-mutated mice were used. Sedation was assessed in triple (H→R) point-mutated mice, in which all GABA$_A$Rs except α1 had been rendered BDZ-insensitive. Conversely, antihyperalgesia was studied in GABA$_A$R α1 (H→R) point-mutated mice to rule out confounding sedation. Dose response curves for DZP showed difference in ED$_{50}$ values strongly favoring sedation (0.59±0.08 mg kg$^{-1}$) over antihyperalgesia (3.4±1.3 mg kg$^{-1}$). By contrast, NDMC exhibited a slight preference for antihyperalgesia over sedation with ED$_{50}$ values of 3.4±0.8 mg kg$^{-1}$ and 3.1±0.9 mg kg$^{-1}$ for sedation and antihyperalgesia, respectively. Therefore, it shows that while DZP induced half-maximal sedation at doses much lower than those required for antihyperalgesia, NDMC elicited both actions with similar dose-dependencies with slight preference for antihyperalgesia over sedation. Further, more importantly, dose response curves for DZP showed that maximum sedation is achieved at lower DZP dose as compared to DZP dose needed to achieve maximum analgesia. By contrast, dose response curves for NDMC showed that maximum sedation is achieved at higher NDMC dose as compared to NMDC dose needed to achieve maximum analgesia.

Altogether those data support that, surprisingly, NDMC possesses not only an improved α2/α1GABAARs activity ratio in vitro, but also a more favorable in vivo pharmacological profile than classical BDZ. In particular, NDMC exhibited even stronger efficacy at α2β3γ2GABA$_A$Rs than the full agonist DZP. A correlation of α2GABA$_A$R occupancy and antihyperalgesic effects performed for DZP indicates that significant analgesia (>50% maximum possible effect) is only achieved at about 70% receptor occupancy even when a full agonist is used (Ralvenius et al., 2015, supra). This may indicate a relevant limitation of subtype selective agonists with only partial agonistic activity at α2GABA$_A$Rs and therefore the limitations encountered by products in development such as L-838,417, TPA023 or TPA023B which failed to enter clinical phases.

By contrast, compared to these compounds, NDMC has a less favorable selectivity ratio but surprisingly much higher activity at α2GABA$_A$Rs leading to the advantageous therapeutic window for the treatment of chronic pain disorders.

The invention claimed is:

1. A method of treating or ameliorating a chronic pain disorder, said method comprising directly administering in a subject in need thereof a therapeutically effective amount of N-desmethylclobazam, a pharmaceutically acceptable salt thereof or a pharmaceutical formulation thereof, alone or in combination with at least one anti-hyperalgesic agent.

2. The method according to claim 1, wherein the chronic pain disorder is neuropathic pain.

3. The method according to claim 1, wherein the chronic pain disorder is fibromyalgia.

4. The method according to claim 1, wherein N-desmethylclobazam or a pharmaceutically acceptable salt is administered in combination with at least one anti-hyperalgesic agent.

5. The method according to claim 4, wherein said at least one anti-hyperalgesic agent is an N-methyl D-aspartate (NMDA) antagonist.

6. The method according to claim 1, wherein said pharmaceutical formulation is a pharmaceutical formulation comprising N-desmethylclobazam or a pharmaceutically acceptable salt thereof combined with at least one an anti-hyperalgesic agent, and at least one pharmaceutically acceptable carrier.

7. The method according to claim 1, wherein the anti-hyperalgesic agent is an N-methyl D-aspartate (NMDA) antagonist.

8. The method according to claim 5, wherein said N-methyl D-aspartate (NMDA) antagonist is selected from the group consisting of ketamine, methadone, memantine, amantadine and dextromethorphan.

9. The method according to claim 1, wherein the subject is a human.

10. The method according to claim 1, wherein the therapeutically effective amount of N-desmethylclobazam, a pharmaceutically acceptable salt thereof or a pharmaceutical formulation thereof is administered at a daily dose of about 5 mg to about 40 mg and the subject is a human.

11. The method according to claim 1, wherein the therapeutically effective amount of N-desmethylclobazam, a pharmaceutically acceptable salt thereof or a pharmaceutical formulation thereof NDMC is administered at a daily dose of about 0.07 mg/kg to about 0.8 mg/kg and the subject is a human.

12. The method according to claim 1, wherein the therapeutically effective amount of N-desmethylclobazam, a pharmaceutically acceptable salt thereof or a pharmaceutical formulation thereof is administered in an amount of about 10 mg to about 120 mg and the subject is a human.

13. The method according to claim 1, wherein the therapeutically effective amount of N-desmethylclobazam, a pharmaceutically acceptable salt thereof or a pharmaceutical formulation thereof is administered in an amount of that achieves a plasma concentration of about 100 to about 2500 ng/ml in a human subject.

14. The method according to claim 1, wherein the therapeutically effective amount of N-desmethylclobazam, a pharmaceutically acceptable salt thereof or a pharmaceutical formulation thereof is administered in a non-sedating amount to a human subject.

15. The method according to claim 10, wherein the therapeutically effective amount of N-desmethylclobazam, a pharmaceutically acceptable salt thereof or a pharmaceutical formulation thereof is administered in a non-sedating amount.

16. The method according to claim 11, wherein the therapeutically effective amount of N-desmethylclobazam, a pharmaceutically acceptable salt thereof or a pharmaceutical formulation thereof is administered in a non-sedating amount.

17. The method according to claim 12, wherein the therapeutically effective amount of N-desmethylclobazam, a pharmaceutically acceptable salt thereof or a pharmaceutical formulation thereof is administered in a non-sedating amount.

18. The method according to claim 13, wherein the therapeutically effective amount of N-desmethylclobazam, a pharmaceutically acceptable salt thereof or a pharmaceutical formulation thereof is administered in a non-sedating amount.

\* \* \* \* \*